US008901113B2

(12) United States Patent
Leech et al.

(10) Patent No.: US 8,901,113 B2
(45) Date of Patent: Dec. 2, 2014

(54) METHODS AND COMPOSITIONS FOR DETERRING ABUSE

(75) Inventors: Ronald L. Leech, Plymouth, IN (US); Rachelle L. Hall Yung, Argos, IN (US); Albert W. Brzeczko, Baltimore, MD (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 516 days.

(21) Appl. No.: 12/893,607

(22) Filed: Sep. 29, 2010

(65) Prior Publication Data

US 2011/0077238 A1 Mar. 31, 2011

Related U.S. Application Data

(60) Provisional application No. 61/247,225, filed on Sep. 30, 2009, provisional application No. 61/304,108, filed on Feb. 12, 2010.

(51) Int. Cl.

| | | |
|---|---|---|
| A61K 31/5517 | (2006.01) | |
| A61K 31/137 | (2006.01) | |
| A61K 31/4458 | (2006.01) | |
| A61K 31/485 | (2006.01) | |
| A61P 25/30 | (2006.01) | |
| A61P 25/04 | (2006.01) | |
| A61K 9/20 | (2006.01) | |
| A61K 9/16 | (2006.01) | |

(52) U.S. Cl.
CPC ............ *A61K 31/137* (2013.01); *A61K 9/2059* (2013.01); *A61K 31/485* (2013.01); *A61K 31/4458* (2013.01); *A61K 9/1652* (2013.01); *A61K 9/2054* (2013.01); *A61K 31/5517* (2013.01); *A61K 9/2027* (2013.01); *A61K 9/1635* (2013.01)
USPC ........... 514/220; 514/653; 514/648; 514/317; 514/282

(58) Field of Classification Search
USPC ......................... 514/220, 653, 648, 317, 282
See application file for complete search history.

(56) References Cited

U.S. PATENT DOCUMENTS

| | | |
|---|---|---|
| 3,065,143 A | 11/1962 | Christenson et al. |
| 3,260,646 A | 7/1966 | Paulsen et al. |
| 4,070,494 A | 1/1978 | Hoffmeister et al. |
| 4,175,119 A | 11/1979 | Porter |
| 4,221,778 A | 9/1980 | Raghunathan |
| 4,389,393 A | 6/1983 | Schor et al. |
| 4,457,933 A | 7/1984 | Gordon et al. |
| 4,459,278 A | 7/1984 | Porter |
| 4,599,342 A | 7/1986 | LaHann |
| 4,610,870 A | 9/1986 | Jain et al. |
| 4,666,705 A | 5/1987 | DeCrosta et al. |
| 4,801,461 A | 1/1989 | Hamel |
| 4,915,952 A | 4/1990 | Ayer et al. |
| 4,952,402 A | 8/1990 | Sparks |
| 5,059,600 A | 10/1991 | Gawin et al. |
| 5,073,380 A | 12/1991 | Babu |
| 5,075,114 A | 12/1991 | Roche |
| 5,084,278 A | 1/1992 | Mehta |
| 5,098,715 A | 3/1992 | McCabe |
| 5,114,942 A | 5/1992 | Gawin et al. |
| 5,273,758 A | 12/1993 | Royce |
| 5,284,662 A | 2/1994 | Koparkar et al. |
| 5,330,766 A | 7/1994 | Morella et al. |
| 5,405,617 A | 4/1995 | Gowan |
| 5,431,916 A | 7/1995 | White |
| 5,484,606 A | 1/1996 | Dhabhar |
| 5,508,042 A | 4/1996 | Oshlack et al. |
| 5,558,879 A | 9/1996 | Chen |
| 5,654,005 A | 8/1997 | Chen |
| 5,741,524 A | 4/1998 | Staniforth et al. |
| 5,807,579 A | 9/1998 | Vilkov |
| 5,840,337 A | 11/1998 | Cody |
| 5,858,409 A | 1/1999 | Karetny |
| 5,895,663 A | 4/1999 | Irwin et al. |
| 5,916,590 A | 6/1999 | Cody et al. |
| 5,919,481 A | 7/1999 | Cody et al. |
| 5,955,107 A | 9/1999 | Augello |
| 5,968,551 A | 10/1999 | Oshlack et al. |
| 5,997,905 A | 12/1999 | McTeigue |
| 6,024,980 A | 2/2000 | Hoy |
| 6,027,746 A | 2/2000 | Lech |

(Continued)

FOREIGN PATENT DOCUMENTS

| | | |
|---|---|---|
| EP | 1293195 | 3/2003 |
| GB | 1428361 | 3/1976 |

(Continued)

OTHER PUBLICATIONS

Rudnic et al. "Oral Solid Dosage Forms" in Remington's Pharmaceutical Sciences, 18th edition, Gennaro, A. R., Ed., Mack Pub. Co.: Eastman, PA, 1990, pp. 1633-1638 and 1666.
Board of Patent Appeals and Interferences Decision on Appeal mailed Aug. 16, 2010 in U.S. Appl. No. 11/136,636.
Office Action mailed Oct. 6, 2010 in U.S. Appl. No. 12/231,136 of Kumar et al.
Office Action mailed Sep. 11, 2007 in U.S. Appl. No. 11/136,636 of Emigh et al.
Office Action mailed Jun. 14, 2007 in U.S. Appl. No. 11/136,636 of Emigh et al.
Office Action mailed Jan. 23, 2007 in U.S. Appl. No. 11/136,636 of Emigh et al.
Office Action mailed Oct. 30, 2006 in U.S. Appl. No. 11/136,636 of Emigh et al.
Office Action mailed May 30, 2006 in U.S. Appl. No. 10/723,654.
Purdue Pharma. L.P. package inserts pp. 1-10 (OxyiR oral capsules) (printed 1996.2003 and 2007)—see 5012 D (U.S. Appl. No. 11/136,636).

(Continued)

*Primary Examiner* — San-Ming Hui
*Assistant Examiner* — Kathrien Cruz
(74) *Attorney, Agent, or Firm* — Morgan, Lewis & Bockius LLP

(57) ABSTRACT

Effective methods and compositions to deter abuse of pharmaceutical products (e.g., orally administered pharmaceutical products) including but not limited to immediate release, sustained or extended release and delayed release formulations for drugs subject to abuse comprising at least 10% by weight hydroxypropylcellulose; polyethylene oxide; and a disintegrant selected from the group consisting of crospovidone, sodium starch glycolate and croscarmellose sodium; wherein the ratio of hydroxypropylcellulose to polyethylene oxide on a weight basis is between about 10:1 and 1:10.

7 Claims, 1 Drawing Sheet

(56) References Cited

U.S. PATENT DOCUMENTS

| | | |
|---|---|---|
| 6,136,864 A | 10/2000 | Nichols et al. |
| 6,153,621 A | 11/2000 | Hamann |
| 6,197,314 B1 | 3/2001 | Elnig |
| 6,210,710 B1 | 4/2001 | Skinner |
| 6,217,903 B1 | 4/2001 | Skinner |
| 6,228,863 B1 | 5/2001 | Palermo et al. |
| 6,248,363 B1 | 6/2001 | Patel et al. |
| 6,277,409 B1 | 8/2001 | Luber |
| 6,294,192 B1 | 9/2001 | Patel |
| 6,309,663 B1 | 10/2001 | Patel et al. |
| 6,309,668 B1 | 10/2001 | Bastin et al. |
| 6,340,471 B1 | 1/2002 | Kershman et al. |
| 6,352,721 B1 | 3/2002 | Faour |
| 6,358,525 B1 | 3/2002 | Guo |
| 6,359,011 B1 | 3/2002 | Bess et al. |
| 6,375,957 B1 | 4/2002 | Kaiko et al. |
| 6,383,471 B1 | 5/2002 | Chen et al. |
| 6,432,442 B1 | 8/2002 | Buehler |
| 6,471,991 B2 | 10/2002 | Robinson |
| 6,488,963 B1 | 12/2002 | McGinity et al. |
| 6,491,949 B2 | 12/2002 | Faour et al. |
| 6,495,529 B1 | 12/2002 | Booth |
| 6,500,459 B1 | 12/2002 | Chhabra |
| 6,514,531 B1 | 2/2003 | Alaux et al. |
| 6,524,618 B1 | 2/2003 | Kumar et al. |
| 6,541,025 B1 | 4/2003 | Kershman et al. |
| 6,551,617 B1 | 4/2003 | Corbo |
| 6,559,159 B2 | 5/2003 | Carroll et al. |
| 6,572,885 B2 | 6/2003 | Oshlack et al. |
| 6,589,556 B2 | 7/2003 | Cheruki et al. |
| 6,592,901 B2 | 7/2003 | Durig et al. |
| 6,593,367 B1 | 7/2003 | Dewey et al. |
| 6,607,748 B1 | 8/2003 | Lenaerts |
| 6,613,357 B2 | 9/2003 | Faour |
| 6,753,009 B2 | 6/2004 | Luber et al. |
| 6,800,668 B1 | 10/2004 | Odidi |
| 6,814,979 B2 | 11/2004 | Rudnic |
| 6,923,988 B2 | 8/2005 | Patel et al. |
| 6,974,591 B2 | 12/2005 | Kendrup |
| RE39,069 E | 4/2006 | Faous |
| 7,090,867 B2 | 8/2006 | Odidi et al. |
| 7,101,572 B2 | 9/2006 | Santos |
| 7,141,250 B2 | 11/2006 | Oshlack et al. |
| 7,144,587 B2 | 12/2006 | Oshlack et al. |
| 7,157,100 B2 | 1/2007 | Doshi et al. |
| 7,157,103 B2 | 1/2007 | Sackler |
| 7,192,966 B2 | 3/2007 | Mayo-Alvarez |
| 7,201,920 B2 | 4/2007 | Kumar et al. |
| 7,332,182 B2 | 2/2008 | Sackler |
| 7,374,779 B2 | 5/2008 | Chen et al. |
| 7,384,653 B2 | 6/2008 | Wright et al. |
| 7,476,402 B2 | 1/2009 | Kumar et al. |
| 7,510,726 B2 | 3/2009 | Kumar et al. |
| 7,524,515 B2 | 4/2009 | Roberts |
| 7,611,728 B2 | 11/2009 | Kidane |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholamaus et al. |
| 7,879,352 B2 | 2/2011 | Solomon et al. |
| 7,897,179 B2 | 3/2011 | Mulye |
| 7,906,143 B1 | 3/2011 | Odidi |
| 8,114,383 B2 | 2/2012 | Bartholomaus et al. |
| 8,273,798 B2 | 9/2012 | Bausch et al. |
| 8,389,007 B2 | 3/2013 | Wright et al. |
| 8,420,700 B1 | 4/2013 | Bausch et al. |
| 2002/0022057 A1 | 2/2002 | Battey |
| 2002/0119196 A1 | 8/2002 | Parikh |
| 2003/0004177 A1 | 1/2003 | Kao et al. |
| 2003/0021841 A1 | 1/2003 | Matharu |
| 2003/0039691 A1 | 2/2003 | Waterman |
| 2003/0049272 A1 | 3/2003 | Joshi et al. |
| 2003/0049320 A1 | 3/2003 | Bhagwatwar |
| 2003/0050620 A1 | 3/2003 | Odidi |
| 2003/0059471 A1 | 3/2003 | Compton |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler et al. |
| 2003/0096791 A1 | 5/2003 | Gupte |
| 2003/0099711 A1 | 5/2003 | Meadows |
| 2003/0124061 A1 | 7/2003 | Roberts et al. |
| 2003/0124185 A1 | 7/2003 | Oshlack et al. |
| 2003/0125347 A1 | 7/2003 | Anderson et al. |
| 2003/0170181 A1 | 9/2003 | Midha |
| 2003/0180362 A1 | 9/2003 | Park |
| 2003/0232081 A1 | 12/2003 | Doshi et al. |
| 2004/0081695 A1 | 4/2004 | Sowden |
| 2004/0109889 A1 | 6/2004 | Bunick |
| 2004/0131552 A1 | 7/2004 | Boehm |
| 2004/0151791 A1 | 8/2004 | Mayo-Alvarez et al. |
| 2004/0185097 A1 | 9/2004 | Kannan |
| 2004/0228802 A1 | 11/2004 | Chang et al. |
| 2004/0265372 A1 | 12/2004 | Wynn et al. |
| 2005/0013857 A1 | 1/2005 | Fu |
| 2005/0020613 A1 | 1/2005 | Boehm et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0163851 A1 | 7/2005 | Feleder |
| 2006/0003007 A1 | 1/2006 | Odidi et al. |
| 2006/0008527 A1 | 1/2006 | Lagoviyer |
| 2006/0013876 A1 | 1/2006 | Lohray |
| 2006/0018837 A1 | 1/2006 | Preston et al. |
| 2006/0029661 A1 | 2/2006 | Radhakruhnan |
| 2006/0057210 A1 | 3/2006 | Oshlack et al. |
| 2006/0093631 A1 | 5/2006 | Buehler |
| 2006/0110327 A1 | 5/2006 | Emigh et al. |
| 2006/0177380 A1 | 8/2006 | Emigh et al. |
| 2007/0042044 A1 | 2/2007 | Fischer et al. |
| 2007/0065510 A1 | 3/2007 | Odidi et al. |
| 2007/0134493 A1 | 6/2007 | Meghpara |
| 2007/0215511 A1 | 9/2007 | Mehta |
| 2007/0292510 A1 | 12/2007 | Huang |
| 2008/0014228 A1 | 1/2008 | Darmuzey |
| 2008/0095843 A1 | 4/2008 | Nutalapati |
| 2008/0152595 A1 | 6/2008 | Emigh et al. |
| 2008/0260837 A1 | 10/2008 | Namburi |
| 2008/0287456 A1 | 11/2008 | Roberts |
| 2008/0305166 A1 | 12/2008 | Durig |
| 2008/0312168 A1 | 12/2008 | Pilgaonkar et al. |
| 2008/0312264 A1 | 12/2008 | Arkena-Maric et al. |
| 2008/0317854 A1 | 12/2008 | Arkenau et al. |
| 2009/0004281 A1 | 1/2009 | Nghiem |
| 2009/0005408 A1 | 1/2009 | Arkena-Maric et al. |
| 2009/0081290 A1 | 3/2009 | McKenna et al. |
| 2009/0081291 A1 | 3/2009 | Gin |
| 2009/0098200 A1 | 4/2009 | Temtsin Krayz et al. |
| 2009/0142378 A1 | 6/2009 | Frisbee |
| 2009/0175937 A1 | 7/2009 | Rahmouni et al. |
| 2009/0202634 A1 | 8/2009 | Jans et al. |
| 2009/0208572 A1 | 8/2009 | Dharmadhikari et al. |
| 2009/0208576 A1 | 8/2009 | Gandhi |
| 2009/0311327 A1 | 12/2009 | Roberts |
| 2009/0317355 A1 | 12/2009 | Roth et al. |
| 2010/0010101 A1 | 1/2010 | Cherukuri |
| 2010/0015223 A1 | 1/2010 | Cailly-Dufestel et al. |
| 2010/0015224 A1 | 1/2010 | Singh |
| 2010/0092555 A1 | 4/2010 | Wynn et al. |
| 2010/0151028 A1 | 6/2010 | Ashworth et al. |
| 2010/0249045 A1 | 9/2010 | Babul |
| 2010/0255063 A1 | 10/2010 | Andersen |
| 2010/0260842 A1 | 10/2010 | Nair |
| 2010/0266666 A1 | 10/2010 | Andersen |
| 2010/0297031 A1 | 11/2010 | beda Perez et al. |
| 2010/0330150 A1 | 12/2010 | Venkatesh |
| 2011/0020440 A1 | 1/2011 | Modi |
| 2011/0028456 A1 | 2/2011 | Lulla |

(56) References Cited

U.S. PATENT DOCUMENTS

| | | |
|---|---|---|
| 2011/0077238 A1 | 3/2011 | Leech |
| 2011/0207761 A1 | 8/2011 | Losev et al. |
| 2013/0065885 A1 | 3/2013 | Roberts et al. |

FOREIGN PATENT DOCUMENTS

| | | |
|---|---|---|
| WO | 9533446 | 5/1995 |
| WO | 9525506 | 9/1995 |
| WO | 9600066 | 1/1996 |
| WO | 9737689 | 10/1997 |
| WO | 9944591 | 9/1999 |
| WO | 9963970 | 12/1999 |
| WO | 0016750 | 3/2000 |
| WO | 0016751 | 3/2000 |
| WO | 0033835 | 6/2000 |
| WO | 0035295 | 6/2000 |
| WO | 02087512 | 11/2002 |
| WO | 03013481 | 2/2003 |
| WO | 03024430 | 3/2003 |
| WO | 03026743 | 4/2003 |
| WO | 03034991 | 5/2003 |
| WO | 03035041 | 5/2003 |
| WO | 2004026256 | 4/2004 |
| WO | 2004026283 | 4/2004 |
| WO | 2004037259 | 5/2004 |
| WO | 2004038428 | 5/2004 |
| WO | 2005016321 | 2/2005 |
| WO | 2005053587 | 6/2005 |
| WO | 2006104703 | 10/2006 |
| WO | 2007054976 | 5/2007 |
| WO | 2008140459 | 11/2008 |
| WO | 2008140460 | 11/2008 |
| WO | 2009080021 | 7/2009 |
| WO | 2010044736 | 4/2010 |
| WO | 2010070028 | 6/2010 |
| WO | 2011039768 | 4/2011 |

OTHER PUBLICATIONS

Office Action mailed Sep. 15, 2010 in U.S. Appl. No. 11/724,502.
Office Action mailed Apr. 27, 2010 in U.S. Appl. No. 11/287,012.
Wells et al., "Effect of Anionic Surfactants on the Release of Chlorpheniramine Maleate From an Inert, D Heterogeneous Matrix." Drug Development, 18 (2), 1992, pp. 175-186.
Rao et al., "Effect of Sodium Lauryl Sulfate on the Release of Rifampicin from Guar Gum Matrix." Indian Journal of D Pharmaceuticals Science, Sep.-Oct. 2000.
Matschiner et al., "Characterization of Ion Pair Formation Between Erythromycin and Lipophilic Counter Ions." D Pharmazie 50(1995): 462-464.
Supplementary European Search Report from EP Pat. App. No. 04812083.6, dated Aug. 20, 2008.
International Search Report and Written Opinion of the International Search Authority from International Application D No. PCT/US2005/042808, dated Aug. 5, 2008.
International Search Report for PCT/US2010/050723 dated Nov. 23, 2010, 3 pages.
Publication of PCT/US2010/050723 dated Apr. 7, 2011, 47 pages.
Written Opinion for PCT/US2010/050723 dated Nov. 23, 2010, 8 pages.

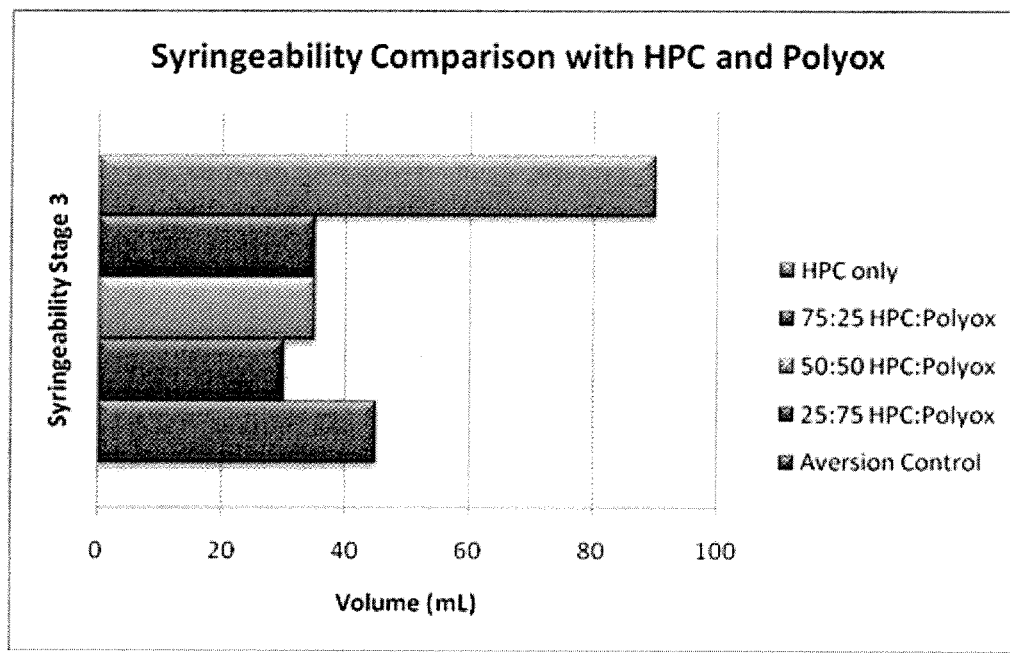

METHODS AND COMPOSITIONS FOR DETERRING ABUSE

RELATED APPLICATIONS

The present application claims priority to U.S. Provisional Patent Application No. 61/247,225, filed Sep. 30, 2009 and U.S. Provisional Patent Application No. 61/304,108 filed Feb. 12, 2010, the disclosure of which are incorporated by reference herein in their entirety.

BACKGROUND

Drug abusers and/or addicts typically may take a solid dosage form intended for oral administration containing one or more active drugs and crush, shear, grind, chew, dissolve and/or heat, extract or otherwise tamper with or damage the dosage form so that a significant portion or even the entire amount of the active drug becomes available for administration.

There are various routes of administration an abuser may commonly employ to abuse a drug containing formulation. The most common methods include 1) parenteral (e.g. intravenous injection), 2) intranasal (e.g., snorting), and 3) repeated oral ingestion of excessive quantities, for example, of orally administered tablets or capsules. One mode of abuse of oral solid drugs involves the extraction of the active component from the dosage form by first mixing the dosage form with a suitable solvent (e.g., water), and then subsequently extracting the active component from the mixture for use in a solution suitable for intravenous injection of the drug to achieve a "high."

Alternatively, an abuser may convert a precursor compound found in a dosage form, such as pseudophedrine or ephedrine to methamphetamine, by illicit chemical processes. Examples of such methods include the Nazi Method, the Red Phosphorus Method, and the Shake and Bake Method.

There is a growing need for novel and effective methods and compositions to deter abuse of pharmaceutical products (e.g., orally administered pharmaceutical products) including but not limited to immediate release, sustained or extended release and delayed release formulations for drugs subject to abuse.

SUMMARY OF THE INVENTION

In certain embodiments, a therapeutic composition includes a drug susceptible to abuse; at least 10% by weight hydroxypropylcellulose; polyethylene oxide; and a disintegrant selected from the group consisting of crospovidone, sodium starch glycolate and croscarmellose sodium. In some embodiments, the ratio of hydroxypropylcellulose to polyethylene oxide on a weight basis is between about 10:1 and 1:10. In some embodiments, the therapeutic composition is an immediate release formulation.

In some embodiments, the drug susceptible to abuse comprises one or more of alfentanil, amphetamines, buprenorphine, butorphanol, carfentanil, codeine, dezocine, dihydrocodeine, dihydromorphine, diphenoxylate, diprenorphine, etorphine, fentanyl, hydrocodone, hydromorphone, β-hydroxy-3-methylfentanyl, levomethadryl, levorphanol, lofentanil, meperidine, methadone, methylphenidate, morphine, nalbuphine, nalmefene, oxycodone, oxymorphone, pentazocine, pethidine, propoxyphene, remifentanil, sufentanil, tilidine and tramodol.

In some embodiments, the hydroxypropylcellulose has a viscosity of about 1,500 mPa·s to about 3,000 mPa·s at 1%. In some embodiments, the hydroxypropylcellulose has a molecular weight of about 1,150,000.

In some embodiments, the polyethylene oxide is present in an amount of about 3 wt % to about 7 wt %. In some embodiments, the polyethylene oxide is present in an amount of about 5.10 wt %. In some embodiments, the crospovidone is present in an amount of about 15 wt % to about 25 wt %; about 18 wt % to about 22 wt %; or about 20.41 wt %.

In some embodiments, the therapeutic composition includes ethylcellulose. In some embodiments, the ethylcellulose has an ethoxyl content of about 45% to about 47%; about 45% to about 51%, or about 47% to about 51%. According to some embodiments, the ethylcellulose has a viscosity of about 70 mPa·s or less. In certain embodiments, the ethylcellulose has a standard ethoxyl content, a high ethoxyl content, or a medium ethoxyl content.

In some embodiments, the therapeutic composition includes a glidant such as, for example, colloidal silicon dioxide. In some embodiments, the therapeutic composition includes a lubricant such as, for example, magnesium stearate.

In some embodiments, the therapeutic composition is a suppository, capsule, caplet, pill, gel, soft gelatin capsule, or compressed tablet form. In some embodiments, the therapeutic composition is in unit dose form.

In certain embodiments, a composition suitable for reducing the chemical conversion of precursor compounds included in the composition to a drug susceptible to abuse includes a precursor compound that can be used in a chemical synthesis of a drug that is susceptible to abuse; at least 10% by weight hydroxypropylcellulose; polyethylene oxide; ethylcellulose and a disintegrant selected from the group consisting of crospovidone, sodium starch glycolate and croscarmellose sodium. In some embodiments, the ratio of hydroxypropylcellulose to polyethylene oxide on a weight basis is between about 10:1 and 1:10. In some embodiments, the precursor compound includes pseudoephedrine. In some embodiments, the composition is an immediate release composition.

BRIEF DESCRIPTION OF THE DRAWING

FIG. 1 shows syringeability results of a composition of the present invention in water.

DETAILED DESCRIPTION OF THE INVENTION

The present invention includes an abuse deterrent formulation for reducing the potential for one or more of a) parenteral abuse, b) inhalation (e.g., by the nasal or oral respiratory route), c) oral abuse of a drug for satisfaction of a physical or psychological dependence, and/or d) extraction of precursor drugs or chemicals which can be further processed to the aforementioned drugs of abuse.

In one embodiment, the present invention deters parenteral abuse by providing a pharmaceutical composition which includes a therapeutically active pharmaceutical, and in particular one or more therapeutically active pharmaceuticals which are susceptible to abuse with one or more gel forming agents such that upon contact with a solvent, the agents swell by absorbing the solvent thereby 1) entrapping the drug in a gel matrix; 2) reducing or preventing a significant amount of the drug from being drawn directly into a syringe; and/or 3) reducing or preventing the extraction of drugs of abuse or their related precursors from being converted to abused drugs.

In some embodiments, the present invention deters abuse as set forth above and also inhibits the ability of an abuser to accomplish a conversion via illicit chemical processes, including but not limited to the Nazi Method, the Red Phosphorus Method, and the Shake and Bake Method.

I. Constituents of an Abuse Deterrent Formulation

A. Drugs Suitable for Use with the Present Invention

Any drug, therapeutically acceptable drug salt, drug derivative, drug analog, drug homologue, or polymorph can be used in the present invention. In one embodiment, the drug is an orally administered drug. In certain embodiments, drugs susceptible to abuse are used. Drugs commonly susceptible to abuse include psychoactive drugs and analgesics, including but not limited to opioids, opiates, stimulants, tranquilizers, narcotics and drugs that can cause psychological and/or physical dependence. In some embodiments, the present invention can include any of the resolved isomers of the drugs described herein, and/or salts thereof.

In some embodiments, a drug for use in the present invention which can be susceptible to abuse can be one or more of the following: alfentanil, amphetamines, buprenorphine, butorphanol, carfentanil, codeine, dezocine, dihydrocodeine, dihydromorphine, diphenoxylate, diprenorphine, etorphine, fentanyl, hydrocodone, hydromorphone, β-hydroxy-3-methylfentanyl, levomethadryl, levorphanol, lofentanil, meperidine, methadone, methylphenidate, morphine, nalbuphine, nalmefene, oxycodone, oxymorphone, pentazocine, pethidine, propoxyphene, remifentanil, sufentanil, tapentadol, tilidine and tramadol, salts, derivatives, analogs, homologues, polymorphs thereof, and mixtures of any of the foregoing.

In some embodiments, the drug for use in the present invention can include norpseudoephedrine, amphetamine-like compounds, amphetamine and methamphetamine precursors including ephedrine, pseudoephedrine, pseudoephedrine HCl, pseudoephedrine sulfate, and phenylpropanolamine, and methyl phenidate or combinations thereof.

In some embodiments, a drug for use with the present invention which can be susceptible to abuse includes one or more of the following: allobarbital, allylprodine, alprazolam, amphetamine, amphetaminil, amobarbital, anileridine, barbital, bezitramide, bromazepam, diazepine, brotizolam, butobarbital, camazepam, cathine/D-norpseudoephedrine, chlordiazepoxide, clobazam, clonazepam, clorazepate, clotiazepam, cloxazolam, cyclobarbital, cyclorphan, cyprenorphine, delorazepam, diampromide, diazepam, dihydromorphine, dimenoxadol, dimephetamol, dimethylthiambutene, dioxaphetyl butyrate, dipipanone, dronabinol, eptazocine, estazolam, ethylloflazepate, etonitrazene, fencamfamine, fenethylline, fenproporex, fludiazepam, flunitrazepam, flurazepam, halazepam, haloxazolam, hydroxypethidine, isomethadone, hydroxymethylmorphinan, ketazolam, ketobemidone, loprazolam, lormetazepam, mazindol, medazepam, meprobamate, meptazinol, metazocine, methaqualone, methylphenobarbital, methyprylon, metopon, midazolam, modafinil, myrophine, narceine, nimetazepam, nordazepam, norlevorphenol, oxazepam, oxazolam, plants and plant parts of the plants belonging to the species Papaver somniferum, papavereturn, pemoline, pentobarbital, phenadoxone, phenomorphan, phenazocine, phenoperidine, piminodine, pholcodeine, phenmetrazine, phentermine, pinazepam, piritramide, prazepam, profadol, proheptazine, promedol, properidine, secbutabarbital, secobarbital, temazepam, tapetadol tetrazepam, tramadol triazolam, vinylbital, each optionally in the form of corresponding stereoisomeric compounds and corresponding derivatives, including esters, ethers, salts and solvates.

In some embodiments, a drug may be present in a therapeutic composition in an amount of about 1 wt % to about 20 wt %; about 1 wt % to about 18 wt %; about 1 wt % to about 16 wt %; about 1 wt % to about 14 wt %; about 1 wt % to about 12 wt %; about 2 wt % to about 10 wt %; about 2 wt % to about 8 wt %; about 3 wt % to about 8 wt %; about 4 wt % to about 7 wt %; about 5 wt % to about 7 wt %, or about 6 wt % to about 7 wt %. In some embodiments, a drug may be present in a therapeutic composition in an amount of about 1 wt %; about 1.5 wt %; about 2 wt %; about 2.5 wt %; about 3 wt %; about 3.5 wt %; about 4 wt %; about 4.5 wt %; about 5 wt %; about 5.5 wt %; about 6 wt %; about 6.5 wt %; about 7 wt %; about 7.5 wt %; about 8 wt %; about 8.5 wt %; about 9 wt %; about 9.5 wt %; about 10 wt %; about 10.5 wt %; about 11 wt %; about 11.5 wt %; about 12 wt %; about 12.5 wt %; about 13 wt %; about 13.5 wt %; about 14 wt %; about 14.5 wt %; about 15 wt %; about 15.5 wt %; about 16 wt %; about 16.5 wt %; about 17 wt %; about 17.5 wt %; about 18 wt %; about 18.5 wt %; about 19 wt %; about 19.5 wt %; or about 20 wt %. In some embodiments, a drug may be present in a therapeutic composition in an amount of about 6.12 wt %.

In some embodiments, a drug is present in a therapeutic composition in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, or about 200 mg.

In some embodiments, a pharmaceutical composition of the present invention includes one or more opioids such as hydrocodone, morphine and oxycodone and/or salts thereof, as the therapeutically active ingredient. Typically when processed into a suitable dosage form, the drug can be present in such dosage forms in an amount normally prescribed, typically about 0.5 to about 25 percent on a dry weight basis, based on the total weight of the formulation.

With respect to analgesics in unit dose form, such an amount can be typically from about 5, 25, 50, 75, 100, 125, 150, 175 or 200 mg. More typically, the drug can be present in an amount from 5 to 500 mg or even 5 to 200 mg. In some embodiments, a dosage form contains an appropriate amount of drug to provide a therapeutic effect.

In some embodiments, the present invention includes one or more constituents which may or may not have pharmacological activity and which are not typically susceptible to abuse in addition to a drug which is susceptible to abuse, described above. In certain embodiments, the one or more constituents which are not typically susceptible to abuse can have an abuse deterrent effect (as described in more detail below) when administered in combination with a drug which is susceptible to abuse. In one embodiment of a dosage form of the present invention which includes a drug that is susceptible to abuse, the one or more additional drugs which can induce an abuse deterrent effect can be included in the dosage form in a sub-therapeutic or sub-clinical amount.

As used herein, "sub-therapeutic" or "sub-clinical" refer to an amount of a referenced substance that if consumed or otherwise administered, is insufficient to induce an abuse deterrent effect (e.g., nausea) in an average subject or is insufficient to meet or exceed the threshold dose necessary for inducing an abuse deterrent effect.

Accordingly, when an embodiment of a dosage form of the present invention is administered in accordance with a health care provider prescribed dosage and/or manner, the one or more additional drugs which can induce an abuse deterrent effect will not be administered in an amount sufficient to induce an abuse deterrent effect. However, when a certain embodiment of the present invention is administered in a dose and/or manner that is different from a health care provider prescribed dose, (i.e., the drug is abused or the dosage form is tampered with) the content of a formulation which can cause an abuse deterrent effect according to the present invention will be sufficient to induce an abuse deterrent effect. Suitable examples of drugs which can be administered in sub-therapeutic amounts in the present invention include niacin, atropine sulfate, homatropine methylbromide, sildenafil citrate, nifedipine, zinc sulfate, dioctyl sodium sulfosuccinate and capsaicin.

B. Viscosity Adjusting/Gel Forming Agents

As described above, the present invention can include one or more viscosity adjusting or gel forming agents (hereafter referred to as gel forming agents) which form a gel upon contact with a solvent.

Suitable gel forming agents include compounds that, upon contact with a solvent, absorb the solvent and swell, thereby forming a viscous or semi-viscous substance that significantly reduces and/or minimizes the amount of free solvent which can contain an amount of solubilized drug, and which can be drawn into a syringe. The viscous or gelled material can also reduce the overall amount of drug extractable with the solvent by entrapping the drug in a gel matrix. In some embodiments, suitable gel forming agents include pharmaceutically acceptable polymers, including hydrophilic polymers, such as hydrogels as well as polymers which are soluble in polar and non-polar organic solvents.

As noted in U.S. Publication No. 2006/0177380 and other references, suitable polymers exhibit a high degree of viscosity upon contact with a suitable solvent. The high viscosity can enhance the formation of highly viscous gels when attempts are made by an abuser to crush and dissolve the contents of a dosage form in an aqueous vehicle and inject it intravenously.

More specifically, in certain embodiments the polymeric material forms a viscous or gelled material upon tampering. In such embodiments, when an abuser crushes and adds solvent to the pulverized dosage form, a gel matrix is formed. The gel matrix acts as both a physical barrier that discourages the abuser from injecting the gel intravenously or intramuscularly by preventing the abuser from transferring sufficient amounts of the solution to a syringe to cause a desired "high" once injected. In some embodiments, the increase in viscosity of the solution discourages the use of legitimate, over the counter, and/or prescription drugs that are included in embodiments of the present invention in the illicit manufacture of other highly abused drugs. Specifically, the gel restricts the solubilization of the drug prior to the conversion of the drug to another drug, e.g., the illicit use of pseudoephedrine in the manufacture of methamphetamine or methcathinone, as described below.

In certain embodiments, suitable polymers include one or more pharmaceutically acceptable polymers selected from any pharmaceutical polymer that will undergo an increase in viscosity upon contact with a solvent, e.g., as described in U.S. Pat. No. 4,070,494, the entire content of which is hereby incorporated by reference. Suitable polymers can include alginic acid, polyacrylic acid, karaya gum, tragacanth, polyethylene oxide, polyvinyl alcohol, hydroxypropylcellulose, and methyl cellulose including sodium carboxy methyl cellulose, hydroxyethyl methyl cellulose hydroxypropyl methyl cellulose and carbomers. In some embodiments, the therapeutic composition includes one or more constituents which gel in aqueous solvents. In some embodiments, the therapeutic composition includes one or more constituents which gel in polar and non-polar organic solvents. In some embodiments, the therapeutic composition includes one or more constituents which gel in aqueous solvents and one or more constituents which gel in polar and non-polar organic solvents. In some embodiments, a therapeutic composition includes a combination of: 1) polyethylene oxide, and 2) hydroxypropylcellulose and/or ethylcellulose.

1. Constituent which Gels in Aqueous Solvents

In some embodiments, the therapeutic composition includes one or more constituents which gel in an aqueous solvent. Examples of suitable polymers include but are not limited to copovidone, methylcellulose, carbomer, carboxymethylcellulose sodium, ceratonia, gelatin, guar gum, hydroxyethyl cellulose, hydroxyethylmethyl cellulose, hydroxypropyl cellulose, hypromellose, methylcellulose, polyethylene oxide, povidone, sodium hyaluronate, and xanthan gum as well as suitable pH dependent polymers which include but are not limited to sodium alginate, hypromellose acetate succinate, hypromellose phthalate, cellulose acetate phthalate, chitosan, polymethacrylates such as but not limited to poly(butyl metacrylate, (2-dimethylyaminoethyly)methacrylate, methyl methacrylate) and poly(methacrylicacid, ethylacrylate), and poly(methyl vinyl ether/maleic acid).

In some embodiments, the therapeutic composition includes polyethylene oxide. In certain embodiments, the polyethylene oxide can have an average molecular weight ranging from about 300,000 to about 5,000,000; about 600,000 to about 5,000,000; about 800,000 to about 5,000,000; about 1,000,000 to about 5,000,000; about 3,000,000 to about 5,000,000; about 3,000,000 to about 8,000,000; and preferably at least about 5,000,000. In one embodiment, the polyethylene oxide includes a high molecular weight polyethylene oxide.

In one embodiment, the average particle size of the polyethylene oxide ranges from about 840 to about 2,000 microns. In another embodiment, the density of the polyethylene oxide can range from about 1.15 to about 1.26 g/ml. In another embodiment, the viscosity can range from about 8,800 to about 17,600 mPa·s.

A suitable polyethylene oxide used in a directly compressible formulation of the present invention may be a homopolymer having repeating oxyethylene groups, i.e., —(—O—$CH_2$—$CH_2$—)$_n$—, where n can range from about 2,000 to about 180,000. In some embodiments, the polyethylene oxide is a commercially available and pharmaceutically acceptable homopolymer having moisture content of no greater than about 1% by weight. Examples of suitable, commercially available polyethylene oxide polymers include Polyox®, WSRN-1105 and/or WSR-coagulant, available from Dow Chemicals Co. In another embodiment, the polymer can be a copolymer, such as a block copolymer of PEO and PPO. In some embodiments, the polyethylene oxide powdered polymers can contribute to a consistent particle size in a directly compressible formulation and eliminate the problems of lack of content uniformity and possible segregation.

In some embodiments, a therapeutic composition includes polyethylene oxide in an amount of about 1 wt % to about 10 wt %; about 1.5 wt %; to about 9 wt %; about 1.5 wt %; to about 8.5 wt %; about 2 wt % to about 8 wt %; about 2.5 wt % to about 7.5 wt %; about 3 wt % to about 7 wt %; about 3.5 wt % to about 6.5 wt %; about 4 wt % to about 6 wt %; about 4.5 wt % to about 5.5 wt %; or about 5 wt % to about 5.5 wt %.

In some embodiments, a therapeutic composition includes polyethylene oxide in an amount of about 1 wt %; about 1.5 wt % about 2 wt %; about 2.5 wt %; about 3 wt %; about 3.5 wt %; about 4 wt %; about 4.5 wt %; about 4.6 wt %; about 4.7 wt %; about 4.8 wt %; about 4.9 wt %; about 5.0 wt %; about 5.1 wt %; about 5.2 wt %; about 5.3 wt %; about 5.4 wt %; about 5.5 wt %; about 5.6 wt %; about 5.7 wt %; about 5.8 wt %; about 5.9 wt %; about 6 wt %; about 6.5 wt %; about 7 wt %; about 7.5 wt %; 8 wt %; about 8.5 wt %; about 9 wt %; about 9.5 wt %; or about 10 wt %.

In some embodiments, a therapeutic composition includes polyethylene oxide in an amount of about 5 mg to about 55 mg; about 5 mg to about 50 mg; about 5 mg to about 45 mg; about 10 mg to about 40 mg; about 15 mg to about 35 mg; or about 20 mg to about 30 mg. In some embodiments, a therapeutic composition includes polyethylene oxide in an amount of about 5 mg; about 10 mg; about 15 mg; about 30 mg; about 40 mg; about 45 mg; about 50 mg; or about 55 mg.

2. Constituent which Gels in Polar and Non-Polar Organic Solvent

In some embodiments, the therapeutic composition includes one or more constituents which gel in one or more polar and/or non-polar organic solvent.

a. Hydroxypropylcellulose

In some embodiments, the therapeutic composition includes hydroxypropylcellulose. While hydroxypropylcellulose can form a gel when in contact with water, it also forms a gel when in contact with polar organic solvents, particularly certain dry organic solvents, e.g., ethyl alcohol.

In some embodiments, suitable hydroxypropylcellulose has a molecular weight of about 600,000 to about 1,300,000; about 1,000,000 to about 1,300,000; about 1,100,000 to about 1,200,000; or about 1,150,000.

As noted above, high viscosity can enhance the formation of highly viscous gels when attempts are made by an abuser to crush and dissolve the contents of a dosage form in an aqueous vehicle and inject it intravenously. However, in certain embodiments, it has been found that in the context of abuse deterrence selection of a lower viscosity hydroxypropylcellulose is suitable.

Accordingly, in certain embodiments, suitable hydroxypropylcellulose has a viscosity of about 1,500 mPa·s to about 6,500 mPa·s; about 2,000 mPa·s to about 6,500 mPa·s; about 2,500 mPa·s to about 6,500 mPa·s; about 3,000 mPa·s to about 6,500 mPa·s; about 3,500 mPa·s to about 6,500 mPa·s; about 4,000 mPa·s to about 6,500 mPa·s; about 4,500 mPa·s to about 6,000 mPa·s; about 5,000 mPa·s to about 5,500 mPa·s; about 1,500 mPa·s to about 3,000 mPa·s; about 2,000 mPa·s to about 2,500 mPa·s; about 1,500 mPa·s to about 3,500 mPa·s; about 1,500 mPa·s to about 4,000 mPa·s; about 1,500 mPa·s to about 4,500 mPa·s; about 1,500 mPa·s to about 5,000 mPa·s; about 1,500 mPa·s to about 5,500 mPa·s; or about 1,500 to about 6,000 mPa·s. In some embodiments, suitable hydroxypropylcellulose has a viscosity of about 1,500 mPa·s; about 1,750 mPa·s, about 2,000 mPa·s; about 2,250 mPa·s; about 2,500 mPa·s; about 2,750 mPa·s; about 3,000 mPa·s; about 3,500 mPa·s; about 4,000 mPa·s; about 4,500 mPa·s; about 5,000 mPa·s; about 5,500 mPa·s; about 6,000 mPa·s; or about 6,500 mPa·s. The viscosity may be measured by a Brookfield viscometer.

In some embodiments, suitable hydroxypropylcellulose has a $D^{50}$ particle size of about 400 μm to about 1,000 μm, about 800 μm to about 1,000 μm; about 850 μm to about 950 μm; about 900 μm to about 950 μm; about 900 μm to about 930 μm; about 910 μm to about 920 μm; about 400 μm to about 650 μm; about 450 μm to about 600 μm; about 500 μm to about 550 μm; or about 510 μm to about 530 μm. In some embodiments, suitable hydroxypropylcellulose has a $D^{50}$ particle size of about 400 μm; about 425 μm; about 450 μm; about 475 μm; about 500 μm; about 501 μm; about 502 μm; about 503 μm; about 504 μm; about 505 μm; about 506 μm; about 507 μm; about 508 μm; about 509 μm; about 510 μm; about 511 μm; about 512 μm; about 513 μm; about 514 μm; about 515 μm; about 516 μm; about 517 μm; about 518 μm; about 519 μm; about 520 μm; about 521 μm; about 522 μm; about 523 μm; about 524 μm; about 525 μm; about 526 μm; about 527 μm; about 528 μm; about 529 μm; about 530 μm; about 531 μm; about 532 μm; about 533 μm; about 534 μm; about 535 μm; about 536 μm; about 537 μm; about 538 μm; about 539 μm; about 540 μm; about 550 μm; about 575 μm; about 600 μm; about 625 μm; about 650 μm; about 675 μm; about 700 μm; about 725 μm; about 750 μm; about 775 μm; about 800 μm; about 825 μm; about 850 μm; about 875 μm; about 900 μm; about 925 μm; about 950 μm; about 975 μm; or about 1000 μm.

In certain embodiments, suitable hydroxypropylcellulose has a tap density of about 0.493 g/cm$^3$ to about 0.552 g/cm$^3$; about 0.498 g/cm$^3$ to about 0.547 g/cm$^3$; about 0.503 g/cm$^3$ to about 0.542 g/cm$^3$; about 0.508 g/cm$^3$ to about 0.537 g/cm$^3$; about 0.493 g/cm$^3$ to about 0.523 g/cm$^3$; about 0.498 g/cm$^3$ to about 0.518 g/cm$^3$; about 0.503 g/cm$^3$ to about 0.513 g/cm$^3$; or about 0.506 g/cm$^3$ to about 0.51 g/cm$^3$. In some embodiments, suitable hydroxypropylcellulose has a tap density of about 0.493 g/cm$^3$; about 0.498 g/cm$^3$; about 0.503 g/cm$^3$; about 0.504 g/cm$^3$; about 0.505 g/cm$^3$; about 0.506 g/cm$^3$; about 0.507 g/cm$^3$; about 0.508 g/cm$^3$; about 0.509 g/cm$^3$; about 0.510 g/cm$^3$; about 0.511 g/cm$^3$; about 0.512 g/cm$^3$; about 0.517 g/cm$^3$; about 0.522 g/cm$^3$; about 0.527 g/cm$^3$; about 0.532 g/cm$^3$; about 0.537 g/cm$^3$; about 0.542 g/cm$^3$; about 0.547 g/cm$^3$; about 552 g/cm$^3$.

An example of suitable, commercially available hydroxypropylcellulose includes Klucel® Hydroxypropylcellulose from Ashland Aqualon Functional Ingredients.

Hydroxypropylcellulose is known in industry (like polyethylene oxide) as a polymer that is used in drug product matrices for creating a sustained release profile. In sustained release forms, the typical concentrations range from about 15% to about 35% hydroxypropylcellulose. In certain embodiments, the present invention can include about 20% to about 40% hydroxypropylcellulose without compromising immediate release characteristics. Immediate release characteristics are understood to include the release of an active promptly after administration.

In some embodiments, a therapeutic composition includes hydroxypropylcellulose in an amount of about 5 wt % to about 35 wt %; about 10 wt % to about 20 wt %; about 15 wt % to about 25 wt %; about 18 wt % to about 22 wt %; or about 19 wt % to about 21 wt %, or about 20% to about 40%. In some embodiments, a therapeutic composition includes hydroxypropylcellulose in an amount of about 5 wt %; about 6 wt %; about 7 wt %; about 8 wt %; about 9 wt %; about 10 wt %; about 11 wt %; about 12 wt %; about 13 wt %; about 14 wt %; about 15 wt %; about 16 wt %; about 17 wt %; about 18 wt %; about 19 wt %; about 20 wt %; about 21 wt %; about 22 wt %; about 23 wt %; about 24 wt %; about 25 wt %, about 30%, about 33 wt %; 37 wt %; or about 40 wt %. In some embodiments, a therapeutic composition includes hydroxypropylcellulose in an amount of at least about 20 wt %.

In some embodiments, a therapeutic composition includes hydroxypropylcellulose in an amount of about 75 mg to about 125 mg; about 80 mg to about 120 mg; about 85 mg to about 115 mg; about 90 mg to about 110 mg; or about 95 mg to about 105 mg. In some embodiments, a therapeutic composition includes hydroxypropylcellulose in an amount of about 75 mg; about 80 mg; about 85 mg; about 90 mg; about 95 mg; about 100 mg; about 105 mg; about 110 mg; about 115 mg; about 120 mg; or about 125 mg.

b. Ethylcellulose

In some embodiments, a therapeutic composition includes ethylcellulose. In some embodiments, suitable ethylcellulose includes an ethoxyl content, or an ethyoxyl substitution, of about 45% to about 53%; about 45% to about 52.5%; about 45% to about 52%; about 45% to about 51.5%; about 45% to about 51%; about 45% to about 50%; about 45% to about 49%; about 45% to about 48%; about 45% to about 47%; about 47% to about 51%; about 48% to about 51%; about 49% to about 51%; about 48% to about 50%; about 45% to about 47%; about 49.6% to about 51.0%; about 49.6% to about 52.5%; about 48.0% to about 49.5%; about 45.0% to about 46.5%; or about 45.0% to about 47.2%. In some embodiments, suitable ethylcellulose includes an ethoxyl content of about 45.0%; about 45.1%; about 45.2%; about 45.3%; about 45.4%; about 45.5%; about 45.6%; about 45.7%; about 45.8%; about 45.9%; about 46.0%; about 46.1%; about 46.2%; about 46.3%; about 46.4%; about 46.5%; about 46.6%; about 46.7%; about 46.8%; about 46.9%; about 47.0%; about 47.1%; about 47.2%; about 47.3%; about 47.4%; about 47.5%; about 47.6%; about 47.7%; about 47.8%; about 47.9%; about 48.0%; about 48.1%; about 48.2%; about 48.3%; about 48.4%; about 48.5%; about 48.6%; about 48.7%; about 48.8%; about 48.9%; about 49.0%; about 49.1%; about 49.2%; about 49.3%; about 49.4%; about 49.5%; about 49.6%; about 49.7%; about 49.8%; about 49.9%; about 50.0%; about 50.1%; about 50.2%; about 50.3%; about 50.4%; about 50.5%; about 50.6%; about 50.7%; about 50.8%; about 50.9%; about 50.0%; about 51.1%; about 51.2%; about 51.3%; about 51.4%; about 51.5%; about 51.6%; about 51.7%; about 51.8%; about 51.9%; about 52.0%; about 52.1%; about 52.2%; about 52.3%; about 52.4%; about 52.5%; about 52.6%; about 52.7%; about 52.8%; about 52.9%; or about 53.0%.

In some embodiments, ethylcellulose having a high ethoxyl content includes ethoxyl in an amount of about 49.6% to about 51.0%, or about 49.6% to about 52.5%. In some embodiments, ethylcellulose having a standard ethoxyl content includes ethoxyl in an amount of about 48.0% to about 49.5%. In some embodiments, ethylcellulose having a medium ethoxyl content includes ethoxyl in an amount of about 45.0% to about 47.2%, or about 45.0% to about 47.9%. In some embodiments, suitable ethylcellulose has a high ethoxyl content. In some embodiments, suitable ethylcellulose has a standard ethoxyl content. In some embodiments, suitable ethylcellulose has a medium ethoxyl content. As used herein, ethoxyl content is interchangeable with "ethoxyl substitution," sometimes referred to as the grade of the ethylcellulose (e.g., medium, standard, or high grade).

A viscosity value for ethylcellulose may be determined by measuring the viscosity (mPa·s of 5 wt % ethylcellulose in a solution of 80/20 toluene/ethanol. Viscosity values for ethylcellulose may be related to the molecular weight of the ethylcellulose. In some embodiments, a higher molecular weight ethylcellulose is associated with a higher viscosity. In some embodiments, suitable ethylcellulose has a viscosity value of about 75 mPa·s or less; about 70 mPa·s or less; about 65 mPa·s or less; about 60 mPa·s or less; about 55 mPa·s or less; about 50 mPa·s or less; about 45 mPa·s or less; about 40 mPa·s or less; about 35 mPa·s or less; about 30 mPa·s or less; about 25 mPa·s or less; about 20 mPa·s or less; about 19 mPa·s or less; about 18 mPa·s or less; about 17 mPa·s or less; about 16 mPa·s or less; about 15 mPa·s or less; about 14 mPa·s or less; about 13 mPa·s or less; about 12 mPa·s or less; about 11 mPa·s or less; about 10 mPa·s or less; about 9 mPa·s or less; about 8 mPa·s or less; about 7 mPa·s or less; about 6 mPa·s or less; about 5 mPa·s or less; about 4 mPa·s or less; about 3 mPa·s or less; about 2 mPa·s or less; or about 1 mPa·s or less. In some embodiments, suitable ethylcellulose has a viscosity value of about 1 mPa·s to about 75 mPa·s; about 1 mPa·s to about 70 mPa·s; 4 mPa·s to about 70 mPa·s; about 4 mPa·s to about 65 mPa·s; about 4 mPa·s to about 60 mPa·s; about 4 mPa·s to about 55 mPa·s; about 4 mPa·s to about 50 mPa·s; about 4 mPa·s to about 45 mPa·s; about 4 mPa·s to about 40 mPa·s; about 4 mPa·s to about 35 mPa·s; about 4 mPa·s to about 30 mPa·s; about 4 mPa·s to about 25 mPa·s; about 4 mPa·s to about 20 mPa·s; about 4 mPa·s to about 15 mPa·s; about 4 mPa·s to about 14 mPa·s; about 4 mPa·s to about 13 mPa·s; about 4 mPa·s to about 12 mPa·s; about 4 mPa·s to about 11 mPa·s; about 4 mPa·s to about 10 mPa·s; about 4 mPa·s to about 9 mPa·s; about 4 mPa·s to about 8 mPa·s; about 4 mPa·s to about 7 mPa·s; about 5 mPa·s to about 9 mPa·s; or about 6 mPa·s to about 8 mPa·s.

Examples of suitable commercially available ethylcellulose include Ethocel Medium 70 by Dow Chemical Co, and N7 and T10 grade ethylcellulose from Functional Ingredients Ashland Aqualon.

The N7 grade of ethylcellulose from Ashland Aqualon Functional Ingredients used in certain formulations has a low molecular weight and low viscosity in the class of standard ethoxyl substitution. The N7 grade of ethylcellulose has a viscosity of 7 mPa·s. The T10 grade of ethylcellulose from Ashland Aqualon Functional Ingredients used in certain formulations has a low molecular weight and low viscosity, and is in the class of high ethoxyl substitution. The T10 grade of ethylcellulose has a viscosity of 10 mPa·s. Based on conventional understanding, polymers having higher molecular weight and higher viscosity should maximize abuse deterrence because of the better gel forming characteristics in aqueous and polar organic solvents. However, in certain embodiments, it has been found that ethylcellulose with lower molecular weight and lower viscosity provides improved abuse deterrence results.

In some embodiments, a therapeutic composition includes ethylcellulose in an amount of about 15 wt % to about 25 wt %; about 18 wt % to about 22 wt %; or about 19 wt % to about 21 wt %. In some embodiments, a therapeutic composition includes ethylcellulose in an amount of about 15 wt %; about 16 wt %; about 17 wt %; about 18 wt %; about 19 wt %; about 20 wt %; about 21 wt %; about 22 wt %; about 23 wt %; about 24 wt %; or about 25 wt %. In some embodiments, a therapeutic composition includes ethylcellulose in an amount of about 20.41 wt %.

In some embodiments, a therapeutic composition includes ethylcellulose in an amount of about 75 mg to about 125 mg; about 80 mg to about 120 mg; about 85 mg to about 115 mg; about 90 mg to about 110 mg; or about 95 mg to about 105 mg. In some embodiments, a therapeutic composition includes ethylcellulose in an amount of about 75 mg; about 80 mg; about 85 mg; about 90 mg; about 95 mg; about 100 mg; about 105 mg; about 110 mg; about 115 mg; about 120 mg; or about 125 mg.

c. Other Gel Forming Agents

Following the teachings set forth herein, other suitable gel forming agents can include one or more of the following polymers: polyvinyl alcohol, hydroxypropyl methyl cellulose, carbomers, ethylcellulose, cellulose acetate, cellulose acetate propionate, cellulose acetate butyrate, cellulose acetate phthalate and cellulose triacetate, cellulose ether, cellulose ester, cellulose ester ether, and cellulose, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyetlryl methacrylates, cyanoetlryl methacrylate, poly(acrylic acid), poly(methacrylic acid), methacrylic acid alkyl amide copolymer, poly(methyl methacrylate), polymethacrylate, poly(methyl methacrylate)copolymer, polyacrylamide, aminoalkyl methacrylate copolymer, poly(methacrylic acid anhydride), and glycidyl methacrylate copolymers.

Any of the above described polymers can be combined together or combined with other suitable polymers, and such combinations are within the scope of the present invention.

The above described gel forming agents can be optimized in light of the teachings set forth herein as necessary or desired in terms of viscosity, molecular weight, etc. The present invention can be used to manufacture immediate release and controlled drug release formulations. Controlled release formulations can include delayed release, bi-modal and multi-modal release, extended and sustained release oral solid dosage preparations. In some embodiments, immediate release therapeutic compositions of the present invention include polymers associated with controlled release formulations. In some embodiments, an immediate release therapeutic composition of the present invention include polymers associated with controlled release formulations in an amount of at least about 75 wt %; at least about 70 wt %; at least about 65 wt %; at least about 60 wt %; at least about 55 wt %; at least about 50 wt %; at least about 45 wt %; at least about 40 wt %; at least about 35 wt %; at least about 30 wt %; at least about 25 wt %; at least about 20 wt %; at least about 15 wt %; at least about 10 wt %; or at least about 5 wt %.

3. Ratios of Polymers

In some embodiments, a first gelling polymer is present in combination with one or more different gel forming polymers. In certain embodiments, the first gel forming polymer is hydroxypropylcellulose and a second polymer is an ethylene oxide such as polyethylene oxide. In certain embodiments, the first gel forming polymer is ethylcellulose and a second polymer is an ethylene oxide such as polyethylene oxide. In certain embodiments, the first gel forming polymer is hydroxypropylcellulose and a second polymer is ethylcellulose.

In one embodiment, the ratio between a first gel forming polymer and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In some embodiments, two different gel forming polymers can be used. As used herein, "different" can be understood to mean chemically different and/or physically distinct, such as differences in viscosity, particle size, shape, density, etc.

In one embodiment, the ratio between hydroxypropylcellulose and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between ethylcellulose and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between polyethylene oxide and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In one embodiment, the ratio between hydroxypropylcellulose and polyethylene oxide on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between ethylcellulose and polyethylene oxide on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between hydroxypropylcellulose and ethylcellulose on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In other embodiments, the ratio of hydroxypropylcellulose and another gel forming polymer on a weight basis is between or is between about 5:1 and 1:10. In other embodiments, the ratio of hydroxypropylcellulose and another gel forming polymer on a weight basis is between or is between about 4:1 and 1:10. In other embodiments, the ratio of hydroxypropylcellulose and another gel forming polymer on a weight basis is between or is between about 6:1 and 1:10. In other embodiments, the ratio of hydroxypropylcellulose and another gel forming polymer on a weight basis is between or is between about 7:1 and 1:10. In other embodiments, the ratio of hydroxypropylcellulose and another gel forming polymer on a weight basis is between or is between about 8:1 and 1:10. In other embodiments, the ratio of hydroxypropylcellulose and another gel forming polymer on a weight basis is between or is between about 9:1 and 1:10. In other embodiments, the ratio of hydroxypropylcellulose and another gel forming polymer on a weight basis is between or is between about 10:1 and 1:10.

In other embodiments, the ratio of polyethylene oxide and another gel forming polymer on a weight basis is between or is between about 5:1 and 1:10. In other embodiments, the ratio of polyethylene oxide and another gel forming polymer on a weight basis is between or is between about 4:1 and 1:10. In other embodiments, the ratio of polyethylene oxide and another gel forming polymer on a weight basis is between or is between about 6:1 and 1:10. In other embodiments, the ratio of polyethylene oxide and another gel forming polymer on a weight basis is between or is between about 7:1 and 1:10. In other embodiments, the ratio of polyethylene oxide and another gel foaming polymer on a weight basis is between or is between about 8:1 and 1:10. In other embodiments, the ratio of polyethylene oxide and another gel forming polymer on a weight basis is between or is between about 9:1 and 1:10. In other embodiments, the ratio of polyethylene oxide and another gel forming polymer on a weight basis is between or is between about 10:1 and 1:10.

In other embodiments, the ratio of ethylcellulose and another gel forming polymer on a weight basis is between or is between about 5:1 and 1:10. In other embodiments, the ratio of ethylcellulose and another gel forming polymer on a weight basis is between or is between about 4:1 and 1:10. In other embodiments, the ratio of ethylcellulose and another gel forming polymer on a weight basis is between or is between about 6:1 and 1:10. In other embodiments, the ratio of ethylcellulose and another gel forming polymer on a weight basis is between or is between about 7:1 and 1:10. In other embodiments, the ratio of ethylcellulose and another gel forming polymer on a weight basis is between or is between about 8:1 and 1:10. In other embodiments, the ratio of ethylcellulose and another gel forming polymer on a weight basis is between or is between about 9:1 and 1:10. In other embodiments, the ratio of ethylcellulose and another gel forming polymer on a weight basis is between or is between about 10:1 and 1:10.

In certain embodiments, a gel forming polymer which forms a gel in an aqueous solvent is present in combination with a gel forming polymer which forms a gel in a polar and/or non-polar organic solvent. In some embodiments, the ratio between a gel forming polymer which forms a gel in an aqueous solvent and a gel forming polymer which forms a gel in a non-polar solvent on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In other embodiments, the ratio of a gel forming polymer which forms a gel in an aqueous solvent and a gel forming polymer which forms a gel in a polar and/or non-polar organic solvent on a weight basis is between or is between about 5:1 and 1:10. In other embodiments, the ratio of a gel forming polymer which fowls a gel in an aqueous solvent and a gel forming polymer which forms a gel in a polar and/or non-polar organic solvent on a weight basis is between or is between about 4:1 and 1:10. In other embodiments, the ratio of a gel forming polymer which forms a gel in an aqueous solvent and a gel forming polymer which forms a gel in a polar and/or non-polar organic solvent on a weight basis is between or is between about 6:1 and 1:10. In other embodiments, the ratio of a gel forming polymer which forms a gel in an aqueous solvent and a gel forming polymer which forms a gel in a polar and/or non-polar organic solvent on a weight basis is between or is between about 7:1 and 1:10. In other embodiments, the ratio of a gel forming polymer which forms a gel in an aqueous solvent and a gel forming polymer which forms a gel in a polar and/or non-polar organic solvent on a weight basis is between or is between about 8:1 and 1:10. In other embodiments, the ratio of a gel forming polymer which forms a gel in an aqueous solvent and a gel forming polymer which forms a gel in a polar and/or non-polar organic solvent on a weight basis is between or is between about 9:1 and 1:10. In other embodiments, the ratio of a gel forming polymer which fauns a gel in an aqueous solvent and a gel forming polymer which forms a gel in a polar and/or non-polar organic solvent on a weight basis is between or is between about 10:1 and 1:10.

In some embodiments, a composition includes three or more gel forming polymers, wherein the ratio between any two gel forming polymers is in accord with the above ratios.

C. Additional Constituents

The present invention can also optionally include other ingredients to enhance dosage form manufacture from a pharmaceutical composition of the present invention and/or alter the release profile of a dosage forming including a pharmaceutical composition of the present invention, including fillers, disintegrants, glidants, and lubricants.

1. Fillers

Some embodiments of the present invention include one or more pharmaceutically acceptable fillers/diluents. In some embodiments, a therapeutic composition includes any suitable binder or filler. In some embodiments, a therapeutic composition includes microcrystalline cellulose. In some embodiments, suitable microcrystalline cellulose can have an average particle size ranging from 20 to about 200 µm, preferably about 100 µm. In some embodiments, the density ranges from 1.512-1.668 g/cm$^3$. In certain embodiments, suitable microcrystalline cellulose should have molecular weight of about 36,000. Other ingredients can include sugars and/or polyols.

An example of suitable commercially available microcrystalline cellulose includes Avicel PH102 by FMC Corporation.

In some embodiments, a therapeutic composition includes microcrystalline cellulose in an amount of about 20 wt % to about 35 wt %; about 22 wt % to about 32 wt %; about 24 wt % to about 30 wt %; or about 26 wt % to about 28 wt %. In some embodiments, a therapeutic composition includes microcrystalline cellulose in an amount of about 20 wt %; about 21 wt %; about 22 wt %; about 23 wt %; about 24 wt %; about 25 wt %; about 26 wt %; about 27 wt %; about 28 wt %; about 29 wt %; about 30 wt %; about 31 wt %; about 32 wt %; about 33 wt %; about 34 wt %; or about 35 wt %. In some embodiments, a therapeutic composition includes about 26.94 wt %.

In certain embodiments, a therapeutic composition includes microcrystalline cellulose in an amount of about 100 mg to about 160 mg; about 105 mg to about 155 mg; about 110 mg to about 150 mg; about 115 mg to about 145 mg; about 120 mg to about 140 mg; about 125 mg to about 135 mg; or about 120 mg to about 135 mg. In certain embodiments, a therapeutic composition includes microcrystalline cellulose in an amount of about 100 mg; about 105 mg; about 110 mg; about 115 mg; about 120 mg; about 125 mg; about 130 mg; about 135 mg; about 140 mg; about 145 mg; about 150 mg; or 155 mg. In some embodiments, a therapeutic composition includes about 132 mg microcrystalline cellulose.

In some embodiments of the invention, the fillers which can be present at about 10 to 65 percent by weight on a dry weight basis, also function as binders in that they not only impart cohesive properties to the material within the formulation, but can also increase the bulk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

2. Disintegrants

In some embodiments, the present invention can include one or more pharmaceutically acceptable disintegrants. Such disintegrants are known to a skilled artisan. In some embodiments, a therapeutic composition includes crospovidone (such as Polyplasdone® XL) having a particle size of about 400 microns and a density of about 1.22 g/ml. In some embodiments, disintegrants can include, but are not limited to, sodium starch glycolate (Explotab®) having a particle size of about 104 microns and a density of about 0.756 g/ml, starch (e.g., Starch 21) having a particle size of about 2 to about 32 microns and a density of about 0.462 g/ml, and croscarmellose sodium (Ac-Di-Sol) having a particle size of about 37 to about 73.7 microns and a density of about 0.529 g/ml. The disintegrant selected should contribute to the compressibility, flowability and homogeneity of the formulation. Further the disintegrant can minimize segregation and provide an immediate release profile to the formulation. An immediate release drug product is understood in the art to allow drugs to dissolve with no intention of delaying or prolonging dissolution or absorption of the drug upon administration, as opposed to products which are formulated to make the drug available over an extended period after administration. In some embodiments, the disintegrant(s) are present in an amount from about 2 wt % to about 25 wt %.

In some embodiments, a therapeutic composition includes crospovidone in an amount of about 15 wt % to about 25 wt %; about 18 wt % to about 22 wt %; or about 19 wt % to about 21 wt %. In some embodiments, a therapeutic composition includes crospovidone in an amount of about 15 wt %; about 16 wt %; about 17 wt %; about 18 wt %; about 19 wt %;

about 20 wt %; about 21 wt %; about 22 wt %; about 23 wt %; about 24 wt %; or about 25 wt %. In some embodiments, a therapeutic composition includes crospovidone in an amount of about 20.41 wt %.

In some embodiments, a therapeutic composition includes crospovidone in an amount of about 75 mg to about 125 mg; about 80 mg to about 120 mg; about 85 mg to about 115 mg; about 90 mg to about 110 mg; or about 95 mg to about 105 mg. In some embodiments, a therapeutic composition includes crospovidone in an amount of about 75 mg; about 80 mg; about 85 mg; about 90 mg; about 95 mg; about 100 mg; about 105 mg; about 110 mg; about 115 mg; about 120 mg; or about 125 mg.

3. Glidants

In one embodiment, the present invention can include one or more pharmaceutically acceptable glidants, including but not limited to colloidal silicon dioxide. In one embodiment, colloidal silicon dioxide (Cab-O-Sil®) having a density of about 0.029 to about 0.040 g/ml can be used to improve the flow characteristics of the formulation. Such glidants can be provided in an amount of from about 0.1 wt % to about 1 wt %; about 0.2 wt % to about 0.8 wt %; or about 0.2 to about 6 wt %. In some embodiments, a therapeutic composition includes a glidant in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %. In some embodiments, a therapeutic composition includes a glidant in an amount of about 0.41 wt %. In some embodiments, a therapeutic composition includes a glidant in an amount of about 1 mg to about 10 mg; about 1 mg to about 5 mg; or about 1 mg to about 3 mg. In some embodiments, a therapeutic composition includes a glidant in an amount of about 1 mg; about 2 mg; about 3 mg; about 4 mg; about 5 mg; about 6 mg; about 7 mg; about 8 mg; about 9 mg; or about 10 mg.

It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

4. Lubricants

In one embodiment, the present invention can include one or more pharmaceutically acceptable lubricants, including but not limited to magnesium stearate. In some embodiments, magnesium stearate has a particle size of about 450 to about 550 microns and a density of about 1.00 to about 1.80 g/ml. In some embodiments of the present invention, a therapeutic composition includes magnesium stearate having a particle size of from about 5 to about 50 microns and a density of from about 0.1 to about 1.1 g/ml. In certain embodiments, magnesium stearate can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In some embodiments, suitable lubricants are stable and do not polymerize within the formulation once combined. Other lubricants which exhibit acceptable or comparable properties include stearic acid, hydrogenated oils, sodium stearyl fumarate, polyethylene glycols, and Lubritab®.

In certain embodiments, a therapeutic composition includes lubricant in an amount of about 0.1 wt % to about 5 wt %; about 0.1 wt % to about 3 wt %; about 0.1 wt % to about 1 wt %; or about 0.1 wt % to about 0.5 wt %. In some embodiments, a therapeutic composition includes lubricant in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %. In some embodiments, a therapeutic composition includes lubricant in an amount of about 0.5 mg to about 5 mg; about 0.5 mg to about 3 mg; or 0.5 mg to about 1.5 mg. In some embodiments, a therapeutic composition includes lubricant in an amount of about 0.5 mg; about 1 mg; about 1.5 mg; about 2 mg; about 2.5 mg; about 3 mg; about 4 mg; about 5 mg; about 6 mg; about 7 mg; about 8 mg; about 9 mg; or about 10 mg.

In certain embodiments, the most important criteria for selection of the excipients are that the excipients should achieve good content uniformity and release the active ingredient as desired. The excipients, by having excellent binding properties, and homogeneity, as well as good compressibility, cohesiveness and flowability in blended form, minimize segregation of powders in the hopper during direct compression.

II. Methods of Making

In some embodiments, any of the constituents may or may not be sequestered from the other constituents during the manufacturing or in the final dosage form (e.g., tablet or capsule). In some embodiments, one or more of the constituents (e.g., gel forming polymers, including polyethylene oxide, hydroxypropylcellulose, and ethylcellulose, disintegrant, fillers and/or drug susceptible to abuse) may be sequestered. In some embodiments, one or more of the constituents (e.g., gel forming polymers, including polyethylene oxide, hydroxypropylcellulose, and ethylcellulose, disintegrant, fillers and/or drug susceptible to abuse) is blended and/or admixed such that all or a portion of the constituents are in contact with other constituents and/or are not sequestered.

A pharmaceutical composition of the present invention including one or more drug, one or more of gel forming agents, and optionally other ingredients, can be suitably modified and processed to form a dosage form of the present invention. In this manner, an abuse deterrent composition comprising gel forming agents, emetics, and any other optional ingredients can be layered onto, coated onto, applied to, admixed with, formed into a matrix with, and/or blended with a drug and optionally other ingredients, thereby providing a therapeutic composition of the present invention.

Suitable formulations and dosage forms of the present invention include but are not limited to powders, caplets, pills, suppositories, gels, soft gelatin capsules, capsules and compressed tablets manufactured from a pharmaceutical composition of the present invention. The dosage forms can be any shape, including regular or irregular shape depending upon the needs of the artisan.

Compressed tablets including the pharmaceutical compositions of the present invention can be direct compression tablets or non-direct compression tablets. In some embodiments, a dosage form of the present invention can be made by wet granulation, and dry granulation (e.g., slugging or roller compaction). The method of preparation and type of excipients are selected to give the tablet formulation desired physical characteristics that allow for the rapid compression of the tablets. After compression, the tablets must have a number of additional attributes such as appearance, hardness, disintegrating ability, and an acceptable dissolution profile.

Choice of fillers and other excipients typically depend on the chemical and physical properties of the drug, behavior of the mixture during processing, and the properties of the final tablets. Adjustment of such parameters is understood to be within the general understanding of one skilled in the relevant art. Suitable fillers and excipients are described in more detail above.

The manufacture of a dosage form of the present invention can involve direct compression and wet and dry granulation methods, including slugging and roller compaction. In some embodiments, it is preferred to use direct compression techniques because of the lower processing time and cost advantages. In some embodiments, suitable processes may include but are not limited to spray coating, spray drying, electrostatic deposition, coprecipitation and hot melt extrusion.

Accordingly, and as described further below, a directly compressible pharmaceutical composition of the present invention can be designed following the teachings set forth herein that can deter one or more of a) parenteral abuse of a drug, b) inhalation abuse of a drug, c) oral abuse of a drug, and d) conversion of a drug using illicit processes.

Steps for making the compositions or dosage forms include the step of providing one or more drugs described above and an amount of gel forming polymer having a desired molecular weight or viscosity as described above and/or providing a disintegrant and other ingredients in the amounts as described above.

By controlling the molecular weight and/or viscosity of the gel forming polymer, a therapeutic composition suitable for use to deter drug abuse can be formed. In some embodiments, in addition to the routes of abuse noted above, a composition according to the present invention inhibits the conversion of one drug or precursor compound into a drug susceptible to abuse.

III. Abuse Deterrence

In one embodiment, less than or equal to about 95%, 94%, 70%, 60%, 54%, 50%, 45%, 40%, 36%, 32%, 30%, 27%, 20%, 10%, 9%, 6%, 5%, 3%, 2% or 1% of the total amount of a drug susceptible to abuse is recovered from a solvent in contact with a dosage form of the present invention. In one embodiment, none or substantially none of the total amount of a drug susceptible to abuse is recoverable from a solvent in contact with a dosage form of the present invention.

A. Deterring Abuse Via Parenteral, or Intranasal and Excess Consumption

Common methods of abusing a drug containing formulation include 1) parenteral, 2) intranasal, and 3) repeated oral ingestion of excessive quantities of the formulation. In order to discourage such abuse, therapeutic compositions of the present invention may include polymers which exhibit a high degree of viscosity upon contact with a suitable solvent. The increase in viscosity may discourage the abuser from injecting the gel intravenously or intramuscularly by preventing the abuser from transferring sufficient amounts of the solution to a syringe. Similarly, the increase in viscosity discourages the abuser from inhaling.

As noted above, it has been found that in certain embodiments, a lower viscosity polymer will provide improved results.

| Grade | Molecular weight (Da) | Viscosity (mPas) | Particle Shape | Particle Size $D^{50}$ um | Bulk Density (g/cm$^3$) | Tap Density (g/cm$^3$) |
|---|---|---|---|---|---|---|
| MF | 850,000 | 4,000-6,500 at 2% | Fluffy structure | 916 | 0.433 | 0.537 |
| HF | 1,150,000 | 1,500-3,000 at 1% | Rounded with flaws | 520 | 0.404 | 0.508 |

Based on conventional understanding, the hydroxypropylcellulose MF grade, having higher viscosity, should maximize the abuse deterrence characteristics of embodiments of the present invention. However, in certain embodiments, it has been found that the HF grade, having reduced viscosity, provides improved abuse deterrence results.

Moreover, as shown in FIG. 1, the syringeability results in water are significantly improved. Syringeability is understood to mean a qualitative or quantitative measure to describe the injectability of a solution. In FIG. 1, a higher syringeability value correlates with increased abuse resistance. The results show that hydroxypropylcellulose alone provides superior abuse resistance in comparison to the control when exposed to a volume of water.

B. Deterring Conversion Via Illicit Methods

Abusers may also attempt to use legitimate, over the counter, and/or prescription drugs or any type of precursor compounds in the illicit manufacture of other drugs. As used herein, a precursor compound is any compound that can be used as a part of a chemical synthesis to manufacture a drug that is susceptible to abuse. Such precursor compounds typically can be extracted in high yield, and thereby used in a chemical synthesis.

Accordingly, compositions of some embodiments of the present invention may restrict, reduce or diminish the extractability of the drug prior to conversion of the drug to another drug, such as pseudoephedrine from pseudoephedrine dosage forms for eventual use in the manufacture of methamphetamine or methcathinone. In some embodiments, therapeutic compositions of the present invention can inhibit the conversion of pseudoephedrine to methamphetamine or methcathinone by forming a gel barrier when the tablets are contacted with full spectrum of solvents, including non-polar organic solvents, polar organic solvents, and aqueous solvents. Examples of such solvents include, but are not limited to, water and methanol.

Conversion of certain precursor compounds, including pseudoephedrine, to methamphetamine may be attempted by a number of methods, including the Nazi Method, the Red Phosphorous Method, and the Shake and Bake Method. In some embodiments, therapeutic compositions of the present invention inhibit extraction of a precursor compound from the original formulation.

Example 1

In one embodiment, a therapeutic composition includes pseudoephedrine HCl, polyethylene oxide, hydroxypropylcellulose, ethylcellulose, microcrystalline cellulose, crospovidone, colloidal silicon dioxide, and magnesium stearate. The therapeutic composition may include pseudoephedrine HCl in an amount of about 6.12 wt %, polyethylene oxide in an amount of about 5.10 wt %; hydroxypropylcellulose in an amount of about 20.41 wt %; ethylcellulose in an amount of about 20.41 wt %; microcrystalline cellulose in an amount of about 26.94 wt %, crospovidone in an amount of about 20.41 wt %; colloidal silicon dioxide in an amount of about 0.41 wt %; and magnesium stearate in an amount of about 0.20 wt %. A 490 mg tablet of such formulation may include 30 mg pseudoephedrine HCl; 25 mg polyethylene oxide; 100 mg hydroxypropylcellulose; 100 mg ethylcellulose; 132 mg microcrystalline cellulose; 100 mg crospovidone; 2 mg colloidal silicon dioxide; and 1 mg magnesium stearate. In such embodiment, suitable hydroxypropylcellulose has a molecular weight of about 1,150,000 and a viscosity of about 1,500 to about 3,000 mPa·s. Suitable ethylcellulose may have an ethoxyl content of about 45% to about 47%. Such therapeutic composition may provide an immediate release product.

One embodiment of the present invention includes:

| Component | mg per Tablet | % (wt/wt) |
|---|---|---|
| Pseudoephedrine HCl | 30 | 6.12 |
| Polyethylene oxide (Polyox WSR coagulant) | 25 | 5.10 |
| Hydroxypropylcellulose Klucel HF | 100 | 20.41 |
| Ethylcellulose (Ethocel, medium ethoxyl content (70 mPa·s) | 100 | 20.41 |
| Microcrystalline cellulose (Avicel PH102) | 132 | 26.94 |
| Crospovidone (Polyplasdone XL) | 100 | 20.41 |
| Colloidal silicon dioxide (Cab-O-Sil M-5P) | 2 | 0.41 |
| Magnesium Stearate | 1 | 0.20 |
| Total | 490 | 100.00 |

The formulation demonstrates an immediate release product which can inhibit the conversion of pseudoephedrine to methamphetamine or methcathinone by forming a gel barrier when the tablets are contacted with full spectrum of solvents, including non-polar organic solvents, polar organic solvents, and aqueous solvents. Examples of such solvents include, but are not limited to, water, isopropyl alcohol, acetone, and diethyl ether.

Conversion of pseudoephedrine to methamphetamine was evaluated using three known methods—the Nazi Method, the Red Phosphorous Method, and the Shake and Bake Method. An additional conversion method was attempted based on extraction by water at pH 1. Each experiment was conducted using 100 pseudoephedrine tablets of the formulation listed above in this Example. Each attempt demonstrated inhibited ability to recover or convert pseudoephedrine to methamphetamine. The methods and the resulting conversion are described in more detail below.

The Nazi Method Simulation

The Nazi Method is based on extraction with aqueous solvent (water) and is known to be employed in large, medium and small scale production of methamphetamine.

100 pseudoephedrine tablets were ground with a coffee grinder. The powdered pills were then stirred with 500-750 mL of deionized water with a magnetic stir bar for an hour in a beaker. The mixture was filtered through a fluted paper filter or coffee filter. The next step in the Nazi Method is to remove the solvent from the filtrate via distillation to recover the pseudoephedrine solid. In this case, however, no pseudoephedrine was recovered at this stage and the process was ended. No pseudoephedrine was recoverable from the formulation using this water extraction method.

Red Phosphorous Method Simulation

The Red Phosphorus Method is based on extraction with polar organic solvents (methanol) and is known to be employed in large, medium and small scale production of methamphetamine.

100 pseudoephedrine tablets were ground with a coffee grinder. The powdered pills were then stirred with 500-750 mL of methanol with a magnetic stir bar for an hour in a beaker. The mixture was filtered through a fluted paper filter or coffee filter. The next step in the Red Phosphorus Method is to remove the solvent from the filtrate via distillation to recover the pseudoephedrine solid. In this case, however, no pseudoephedrine was recovered at this stage and the process was ended. No pseudoephedrine was recoverable from the formulation using this methanol extraction method.

The Shake and Bake Method Simulation

The Shake and Bake Method is generally known to be employed in small scale (gram quantities) production of methamphetamine using diethyl ether as a non-polar organic solvent.

100 pseudoephedrine tablets were ground with a coffee grinder. The powdered pills were then mixed with ¼ cups (or about 180 mL) of ammonium nitrate. The powder was transferred to a 1 L bottle and combined with 450 mL diethyl ether, ½ bottle cap of crushed sodium hydroxide (gram quantity was recorded), and 1 bottle cap of water (mL quantity was recorded). The bottle was closed and the mixture stirred with a magnetic stir bar for 5 minutes before the pressure was released. ½ caps of crushed sodium hydroxide (gram quantity was recorded) were added every 20 minutes while stirring, until a total of 30 g of sodium hydroxide was added over 2 hours. Next, the mixture was filtered through fluted filter paper into a 1 L flask. Hydrogen chloride gas was bubbled through the filtrate for approximately 1 minute. The precipitated pseudoephedrine hydrochloride was collected by decanting off the liquid or filtration.

The typical yield from commercial product is about 85%. Upon analyzing the dried solid, in different iterations it was found that at most only about 53% of the pseudoephedrine was recovered.

Carte Blanche Simulation

The additional conversion attempt was based on extraction with water at pH 1. 100 pseudoephedrine tablets were ground with a coffee grinder. The powdered pills were then stirred with 250 mL of deionized water in a 1 L beaker with a plastic stir rod. 100 mL of concentrated HCl was added and the mixture was stirred with a magnetic stir bar for 1 hour. The mixture was then filtered through a fluted paper filter or coffee filter. The next step in the method was to remove the solvent from the filtrate via distillation to recover the pseudoephedrine HCl solid. In this case, however, no pseudoephedrine was recovered at this stage and the process was ended. No pseudoephedrine was recoverable from the formulation using this extraction method.

Example 2

In one embodiment, a therapeutic composition includes pseudoephedrine HCl, polyethylene oxide, hydroxypropylcellulose, ethylcellulose, microcrystalline cellulose, crospovidone, colloidal silicon dioxide, and magnesium stearate. The therapeutic composition may include pseudoephedrine HCl in an amount of about 6.1 wt %, polyethylene oxide in an amount of about 5.1 wt %; hydroxypropylcellulose in an amount of about 20.4 wt %; ethylcellulose in an amount of about 20.4 wt %; microcrystalline cellulose in an amount of about 26.94 wt %, crospovidone in an amount of about 20.4 wt %; colloidal silicon dioxide in an amount of about 0.4 wt %; and magnesium stearate in an amount of about 0.2 wt %. A 490 mg tablet of such formulation may include 30 mg pseudoephedrine HCl; 25 mg polyethylene oxide; 100 mg hydroxypropylcellulose; 100 mg ethylcellulose; 132 mg microcrystalline cellulose; 100 mg crospovidone; 2 mg colloidal silicon dioxide; and 1 mg magnesium stearate. In such embodiment, suitable hydroxypropylcellulose has a molecular weight of about 1,150,000 and a viscosity of about 1,500 to about 3,000 mPa·s. Suitable ethylcellulose may have an ethoxyl content of about 48% to about 49.5%. Such therapeutic composition may provide an immediate release product.

One embodiment of the present invention includes:

| Component | mg per Tablet | % (wt/wt) |
|---|---|---|
| Pseudoephedrine HCl | 30 | 6.1 |
| Polyethylene oxide (Polyox WSR Coagulant) | 25 | 5.1 |
| Hydroxypropylcellulose (Klucel HF) | 100 | 20.4 |
| Ethylcellulose (7 mPa · s) (Aqualon N7 grade, standard ethoxy content) | 100 | 20.4 |
| Microcrystalline cellulose Avicel PH102 | 132 | 26.9 |
| Crospovidone (Polyplasdone XL) | 100 | 20.4 |
| Colloidal silicon dioxide (Cab-O-Sil M-5P) | 2 | 0.4 |
| Magnesium Stearate | 1 | 0.2 |
| Total | 490 | 100.0 |

The formulation demonstrates an immediate release product which can inhibit the conversion of pseudoephedrine to methamphetamine or methcathinone by forming a gel barrier when the tablets are contacted with full spectrum of solvents, including non-polar organic solvents, polar organic solvents, and aqueous solvents. Examples of such solvents include, but are not limited to, water, ethanol, acetone, and diethyl ether.

Recovery and conversion of pseudoephedrine to methamphetamine was evaluated using the Nazi Method, the Red Phosphorous Method, and the Shake and Bake Method, as described above. No pseudoephedrine was recoverable from the formulation using any of the three methods to convert to methamphetamine.

Example 3

In one embodiment, a therapeutic composition includes pseudoephedrine HCl, polyethylene oxide, hydroxypropylcellulose, ethylcellulose, microcrystalline cellulose, crospovidone, colloidal silicon dioxide, and magnesium stearate. The therapeutic composition may include pseudoephedrine HCl in an amount of about 6.1 wt %, polyethylene oxide in an amount of about 5.1 wt %; hydroxypropylcellulose in an amount of about 20.4 wt %; ethylcellulose in an amount of about 20.4 wt %; microcrystalline cellulose in an amount of about 26.94 wt %, crospovidone in an amount of about 20.4 wt %; colloidal silicon dioxide in an amount of about 0.4 wt %; and magnesium stearate in an amount of about 0.2 wt %. A 490 mg tablet of such formulation may include 30 mg pseudoephedrine HCl; 25 mg polyethylene oxide; 100 mg hydroxypropylcellulose; 100 mg ethylcellulose; 132 mg microcrystalline cellulose; 100 mg crospovidone; 2 mg colloidal silicon dioxide; and 1 mg magnesium stearate. In such embodiment, suitable hydroxypropylcellulose has a molecular weight of about 1,150,000 and a viscosity of about 1,500 to about 3,000 mPa·s. Suitable ethylcellulose may have an ethoxyl content of about 49.6% to about 51%. Such therapeutic composition may provide an immediate release product.

One embodiment of the present invention includes:

| Component | mg per Tablet | % (wt/wt) |
|---|---|---|
| Pseudoephedrine HCl | 30 | 6.1 |
| Polyethylene oxide (Polyox WSR coagulant) | 25 | 5.1 |
| Hydroxypropylcellulose (Klucel HF) | 100 | 20.4 |
| Ethylcellulose (10 mPa · s) (Aqualon T10 grade, high ethoxyl content) | 100 | 20.4 |
| Microcrystalline cellulose (Avicel PH102) | 132 | 26.9 |
| Crospovidone (Polyplasdone XL) | 100 | 20.4 |
| Colloidal silicon dioxide (Cab-O-Sil M-5P) | 2 | 0.4 |
| Magnesium Stearate | 1 | 0.2 |
| Total | 490 | 100.0 |

The formulation demonstrates an immediate release product which can inhibit the conversion of pseudoephedrine to methamphetamine or methcathinone by forming a gel barrier when the tablets are contacted with full spectrum of solvents, including non-polar organic solvents, polar organic solvents, and aqueous solvents. Examples of such solvents include, but are not limited to, water, isopropyl alcohol, acetone and diethyl ether.

Conversion of pseudoephedrine to methamphetamine was evaluated using the Nazi Method, the Red Phosphorous Method, and the Shake and Bake Method, as described above in Example 1. No pseudoephedrine was recoverable from the formulation using any of the three methods to convert to methamphetamine.

Example 4

Conversion of pseudoephedrine to methamphetamine was evaluated for several formulations using the benchmark Shake and Bake Method, as described above.

| Formulation ID | % Recovered |
|---|---|
| Sudafed | ~76.7 |
| Original Formulation | 42.7-53 |
| PE-EC Formulation G Tablets [PE-EC100AqualonT10 Tablets] | None |
| PE-EC Formulation H Tablets [PE-EC100AqualonN7 Tablets] | None |

Original Formulation is the formulation described in Example 1. Formulation G is the formulation described in Example 3, and Formulation H is the formulation described in Example 2.

Accordingly, formulations described herein including a lower viscosity HPC exhibit enhanced abuse deterrence with respect to syringeability. Such formulations also exhibit an enhanced reduction in the recoverability of compounds that may be used in the synthesis of a drug that is susceptible to abuse. Moreover, formulations described herein including a lower viscosity HPC and a lower viscosity EC exhibit enhanced abuse deterrence with respect to syringeability as well as significantly enhanced reduction in the recoverability of compounds that may be used in the synthesis of a drug that is susceptible to abuse.

For example, while the formulation of Example 1 sufficiently reduces the recovery of pseudoephedrine, Examples 2 and 3 blocked any recovery of pseudoephedrine.

Some minor variations in recovery values may be based on technique and other factors known to one of skill in the art.

In addition to the aforementioned examples 1-4 demonstrating reduced extraction recovery via commonly used extraction and conversion techniques for pseudoephedrine, additional examples of this invention for other drugs of abuse are shown for controlled and immediate release formulations.

Example 5

In one embodiment, a therapeutic composition includes methadone hydrochloride, polyethylene oxide, hydroxypropylcellulose, ethylcellulose, microcrystalline cellulose, crospovidone, citric acid, colloidal silicon dioxide, and magnesium stearate. The therapeutic composition may include methadone HCl in an amount of about 2.0 wt %, polyethylene oxide in an amount of about 5:1 wt %; hydroxypropylcellulose in an amount of about 10.2 wt %; ethylcellulose in an amount of about 10.2 wt %; microcrystalline cellulose in an amount of about 45.4 wt %, crospovidone in an amount of about 20.4 wt %; citric acid in an amount of about 6.1%, colloidal silicon dioxide in an amount of about 0.4 wt %; and magnesium stearate in an amount of about 0.2 wt %. A 490 mg tablet of such formulation may include 10 mg methadone HCl; 25 mg polyethylene oxide; 50 mg hydroxypropylcellulose; 50 mg ethylcellulose; 222 mg microcrystalline cellulose; 100 mg crospovidone; 30 mg citric acid, 2 mg colloidal silicon dioxide; and 1 mg magnesium stearate. In such embodiment, suitable hydroxypropylcellulose has a molecular weight of about 850,000. Suitable ethylcellulose may have an ethoxyl content of about 45. % to about 47% and a viscosity of about 50 mPa·s. Such therapeutic composition may provide an immediate release abuse deterrent product for methadone as well as other drugs of abuse in the opioid analgesic class.

| Component | mg per Tablet | % (wt/wt) |
|---|---|---|
| Methadone HCL | 10 | 2.0 |
| Polyethylene oxide (Polyox WSR 301) | 25 | 5.1 |
| Hydroxypropylcellulose (Klucel MF) | 50 | 10.2 |
| Ethylcellulose (Aqualon K50 grade, medium ethoxyl content (50 mPa · s) | 50 | 10.2 |
| Microcrystalline cellulose (Avicel PH101) | 222 | 45.4 |
| crospovidone (Polyplasdone XL-10) | 100 | 20.4 |
| Citric acid | 30 | 6.1 |
| Cab-O-Sil M-5P colloidal silicon dioxide | 2 | 0.4 |
| Magnesium Stearate | 1 | 0.2 |
| Total | 490 | 100 |

Example 6

In one embodiment, a therapeutic composition includes alprazolam, niacin, polyethylene oxide, hydroxypropylcellulose, microcrystalline cellulose, crospovidone, sodium lauryl sulfate and magnesium stearate. The therapeutic composition may include alprazolam in an amount of about 0.4 wt %, niacin in an amount of about 24.5%, polyethylene oxide in an amount of about 3.1 wt %; hydroxypropylcellulose in an amount of about 20.4 wt %; microcrystalline cellulose in an amount of about 29.6 wt %, crospovidone in an amount of about 20.4 wt %; sodium lauryl sulfate in an amount of about 1.4 wt %; and magnesium stearate in an amount of about 0.2 wt %. A 245 mg tablet of such formulation may include 1 mg alprazolam; 60 mg niacin, 7.5 mg polyethylene oxide; 50 mg hydroxypropylcellulose; 72.5 mg microcrystalline cellulose; 50 mg crospovidone; 3.5 mg sodium lauryl sulfate; and 0.5 mg magnesium stearate. In such embodiment, suitable polyethylene oxide has a suitable molecular weight of about 7,000,000 and hydroxypropylcellulose has a molecular weight of about 1,150,000. Such therapeutic composition may provide an immediate release abuse deterrent product for alprazolam and other drugs of abuse in the benzodiazepine class.

| Component | mg per Tablet | % (wt/wt) |
|---|---|---|
| Alprazolam | 1 | 0.4 |
| Niacin | 60 | 24.5 |
| Polyethylene oxide (Polyox WSR 303) | 7.5 | 3.1 |
| Hydroxypropylcellulose (Klucel HF) | 50 | 20.4 |
| Microcrystalline cellulose (Avicel PH102) | 72.5 | 29.6 |
| Crospovidone (Polyplasdone XL) | 50 | 20.4 |
| Sodium Lauryl Sulfate | 3.5 | 1.4 |
| Magnesium Stearate | 0.5 | 0.2 |
| Total | 245 | 100 |

Example 7

In one embodiment, a therapeutic composition includes methylphenidate hydrochloride, polyethylene oxide, hydroxypropylcellulose, ethylcellulose, microcrystalline cellulose, crospovidone, citric acid, colloidal silicon dioxide, and magnesium stearate. The therapeutic composition may include methylphenidate HCl in an amount of about 5 wt %, polyethylene oxide in an amount of about 5 wt %; hydroxypropylcellulose in an amount of about 20 wt %; ethylcellulose in an amount of about 25 wt %; microcrystalline cellulose in an amount of about 19 wt %, crospovidone in an amount of about 15 wt %; citric acid in an amount of about 10%, colloidal silicon dioxide in an amount of about 0.5 wt %; and magnesium stearate in an amount of about 0.5 wt %. A 400 mg tablet of such formulation may include 20 mg methylphenidate HCl; 20 mg polyethylene oxide; 80 mg hydroxypropylcellulose; 100 mg ethylcellulose; 76 mg microcrystalline cellulose; 60 mg crospovidone; 40 mg citric acid, 2 mg colloidal silicon dioxide; and 2 mg magnesium stearate. In such embodiment, suitable polyethylene oxide has a molecular weight of 1,000,000 and hydroxypropylcellulose has a molecular weight of about 850,000. Suitable ethylcellulose may have an ethoxyl content of about 48% to about 49.5% and a viscosity of about 45 mPa·s. Such therapeutic composition may provide an immediate release abuse deterrent product for methylphenidate as well as other drugs of abuse in the stimulant class.

| Component | mg per Tablet | % (wt/wt) |
|---|---|---|
| Methylphenidate HCL | 20 | 5.0 |
| polyethylene oxide (Polyox WSR N-12K) | 20 | 5.0 |
| hydroxypropylcellulose (Klucel MF) | 80 | 20.0 |
| Ethylcellulose (45 mPa · s) | 100 | 25.0 |

| Component | mg per Tablet | % (wt/wt) |
|---|---|---|
| Ethocel ™ standard 45 premium) | | |
| microcrystalline cellulose (Avicel PH102) | 76 | 19.0 |
| crospovidone (Polyplasdone XL) | 60 | 15.0 |
| Citric Acid | 40 | 10.0 |
| Cab-O-Sil M-5P colloidal silicon dioxide | 2 | 0.5 |
| Magnesium Stearate | 2 | 0.5 |
| Total | 400 | 100 |

Example 8

In one embodiment, a therapeutic composition includes oxymorphone hydrochloride, polyethylene oxide, hydroxypropylcellulose, ethylcellulose, microcrystalline cellulose, crospovidone, colloidal silicon dioxide, and magnesium stearate. The therapeutic composition may include oxymorphone HCl in an amount of about 2.4 wt %, polyethylene oxide in an amount of about 3.6 wt %; hydroxypropylcellulose in an amount of about 23.8 wt %; ethylcellulose in an amount of about 23.8 wt %; microcrystalline cellulose in an amount of about 27.6 wt %, crospovidone in an amount of about 17.8 wt %, colloidal silicon dioxide in an amount of about 0.5 wt %; and magnesium stearate in an amount of about 0.5 wt %. A 420 mg tablet of such formulation may include 10 mg oxymorphone HCl; 15 mg polyethylene oxide; 100 mg hydroxypropylcellulose; 100 mg ethylcellulose; 166 mg microcrystalline cellulose; 75 mg crospovidone; 2 mg colloidal silicon dioxide; and 2 mg magnesium stearate. In such embodiment, suitable polyethylene oxide has a molecular weight of 5,000,000 and hydroxypropylcellulose has a molecular weight of about 1,150,000. Suitable ethylcellulose may have an ethoxyl content of about 49.6% to about 52.5% and a viscosity of about 22 mPa·s. Such therapeutic composition may provide an extended release abuse deterrent product.

| Component | mg per Tablet | % (wt/wt) |
|---|---|---|
| Oxymorphone HCL | 10 | 2.4 |
| polyethylene oxide (Polyox WSR Coagulant) | 15 | 3.6 |
| hydroxypropylcellulose (Klucel HF) | 100 | 23.8 |
| ethylcellulose (22 mPa · s) (Aqualon X22 grade, high ethoxyl content | 100 | 23.8 |
| microcrystalline cellulose (Avicel PH101) | 116 | 27.6 |
| Crospovidone (Polyplasdone XL-10) | 75 | 17.8 |
| colloidal silicon dioxide (Cab-O-Sil M-5P) | 2 | 0.5 |
| Magnesium Stearate | 2 | 0.5 |
| Total | 420 | 100 |

As used herein, the term "about" is understood to mean±10% of the value referenced. For example, "about 45%" is understood to literally mean 40.5% to 49.5%.

A number of references have been cited, the entire disclosures of which are incorporated herein by reference

We claim:

1. A composition suitable for reducing the chemical conversion of precursor compounds included in the composition to a drug susceptible to abuse comprising:
   pseudoephedrine, or a therapeutically acceptable salt thereof;
   at least 10% by weight hydroxypropylcellulose;
   polyethylene oxide; and
   about 2% by weight to about 25% by weight of a disintegrant selected from the group consisting of crospovidone, sodium starch glycolate and croscarmellose sodium;
   wherein the ratio of hydroxypropylcellulose to polyethylene oxide on a weight basis is between about 10:1 and 1:10.

2. The therapeutic composition of claim 1, wherein the composition further comprises ethylcellulose.

3. The therapeutic composition of claim 2, wherein the ethylcellulose includes ethoxyl in an amount of about 48.0% to about 49.5%.

4. The therapeutic composition of claim 2, wherein the ethylcellulose includes ethoxyl in an amount of about 49.6% to about 52.5%.

5. The therapeutic composition of claim 2, wherein the ethylcellulose includes ethoxyl in an amount of about 45.0% to about 47.9%.

6. The composition of claim 1, wherein the hydroxypropylcellulose has a viscosity of about 1,500 mPa·s to about 3,000 mPa·s.

7. The composition of claim 1, wherein the composition is an immediate release composition.

* * * * *